(12) United States Patent
Peterman

(10) Patent No.: US 7,594,919 B2
(45) Date of Patent: Sep. 29, 2009

(54) ARTIFICIAL DISC INSERTER

(75) Inventor: Marc M. Peterman, Memphis, TN (US)

(73) Assignee: Warsaw Orthopedic, Inc.

( * ) Notice: Subject to any disclaimer, the term of this patent is extended or adjusted under 35 U.S.C. 154(b) by 699 days.

(21) Appl. No.: 10/898,032

(22) Filed: Jul. 23, 2004

(65) Prior Publication Data
US 2006/0030860 A1 Feb. 9, 2006

(51) Int. Cl.
A61B 17/56 (2006.01)
A61B 17/70 (2006.01)

(52) U.S. Cl. .................. 606/99; 623/17.14

(58) Field of Classification Search .......... 606/86, 606/99, 246, 279; 623/17.11, 17.14–17.16
See application file for complete search history.

(56) References Cited

U.S. PATENT DOCUMENTS

| | | | | |
|---|---|---|---|---|
| 2,549,731 | A * | 4/1951 | Wattley ............... | 439/482 |
| 3,136,040 | A * | 6/1964 | Bauer et al. .......... | 29/739 |
| 5,782,830 | A * | 7/1998 | Farris ................. | 606/61 |
| 5,951,564 | A * | 9/1999 | Schroder et al. ...... | 606/100 |
| 6,113,639 | A | 9/2000 | Ray et al. | |
| 6,319,257 | B1 * | 11/2001 | Carignan et al. ...... | 606/99 |
| 6,368,325 | B1 | 4/2002 | McKinley et al. | |
| 6,440,133 | B1 | 8/2002 | Beale et al. | |
| 6,478,800 | B1 * | 11/2002 | Fraser et al. ......... | 606/99 |
| 6,540,785 | B1 * | 4/2003 | Gill et al. ............ | 623/17.14 |
| 6,613,091 | B1 | 9/2003 | Zdeblick et al. | |
| 7,235,082 | B2 * | 6/2007 | Bartish et al. ........ | 606/99 |
| 2002/0055745 | A1 | 5/2002 | McKinley et al. | |
| 2003/0018342 | A1 | 1/2003 | Oribe et al. | |
| 2003/0114854 | A1 | 6/2003 | Pavlov et al. | |
| 2003/0149438 | A1 | 8/2003 | Nichols et al. | |
| 2003/0233145 | A1 | 12/2003 | Landry et al. | |
| 2004/0030387 | A1 | 2/2004 | Landry et al. | |
| 2004/0093021 | A1 | 5/2004 | Hanson | |
| 2004/0117022 | A1 | 6/2004 | Marnay et al. | |

FOREIGN PATENT DOCUMENTS

DE 20310433 U1 * 9/2003

OTHER PUBLICATIONS

Patent Cooperation Treaty—European Patent Office, "Notification of Transmittal of the International Search Report and the Written Opinion of the International Searching Authority, or the Declaration." International Application No. PCT/US2005/026286, Nov. 2, 2005, 13 pages.

* cited by examiner

Primary Examiner—Eduardo C Robert
Assistant Examiner—David Comstock

(57) ABSTRACT

An instrument for inserting an implant is provided. The implant includes a protrusion having a protrusion width for extending into a portion of a bone structure. The instrument includes an elongated member and a first member connected to the elongated member. The first member is adapted for selectively engaging the implant. The first member has a width substantially equal to or less than the protrusion width. A second member may be in movable communication with the first member for selectively engaging the implant.

19 Claims, 10 Drawing Sheets

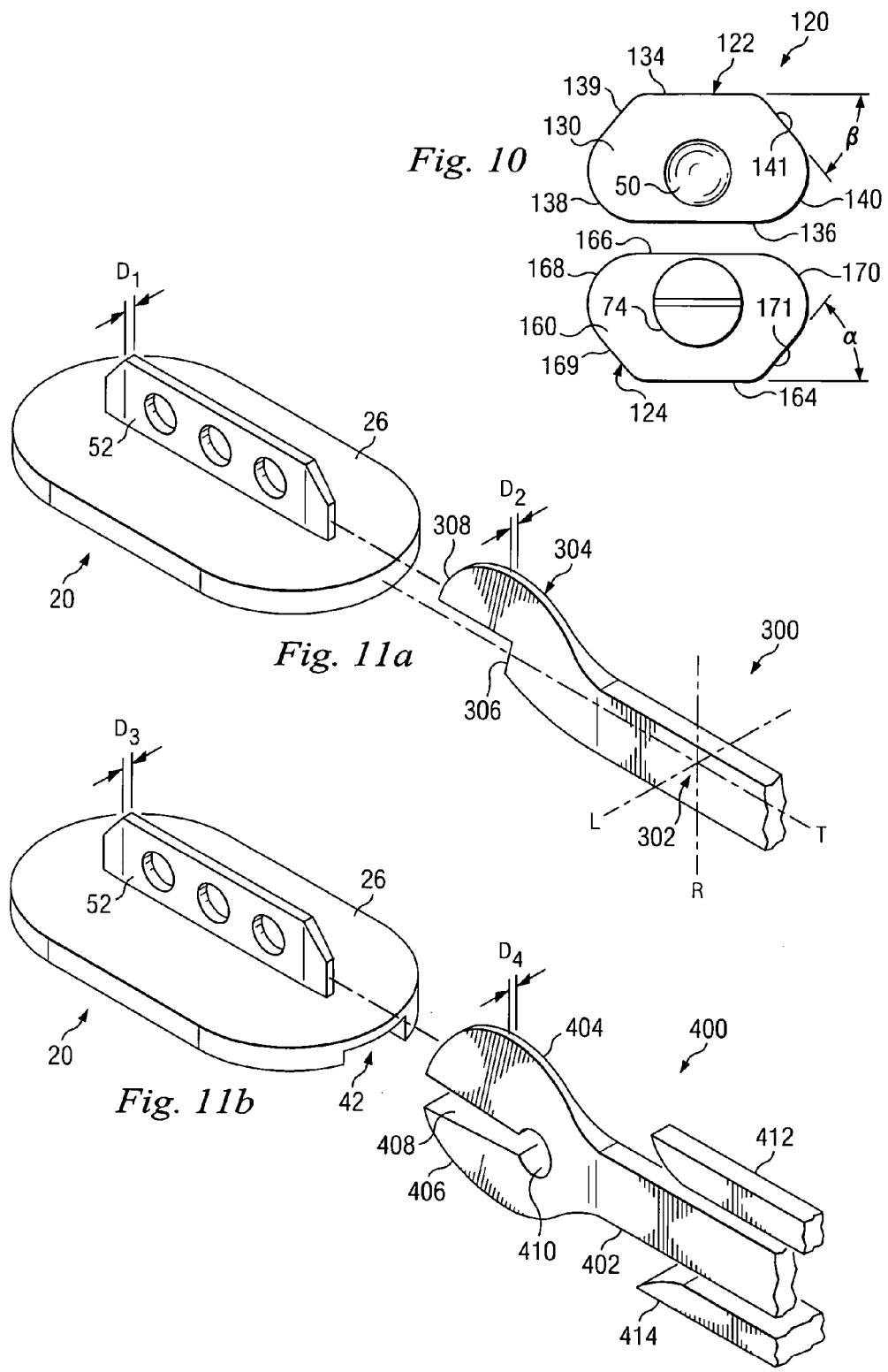

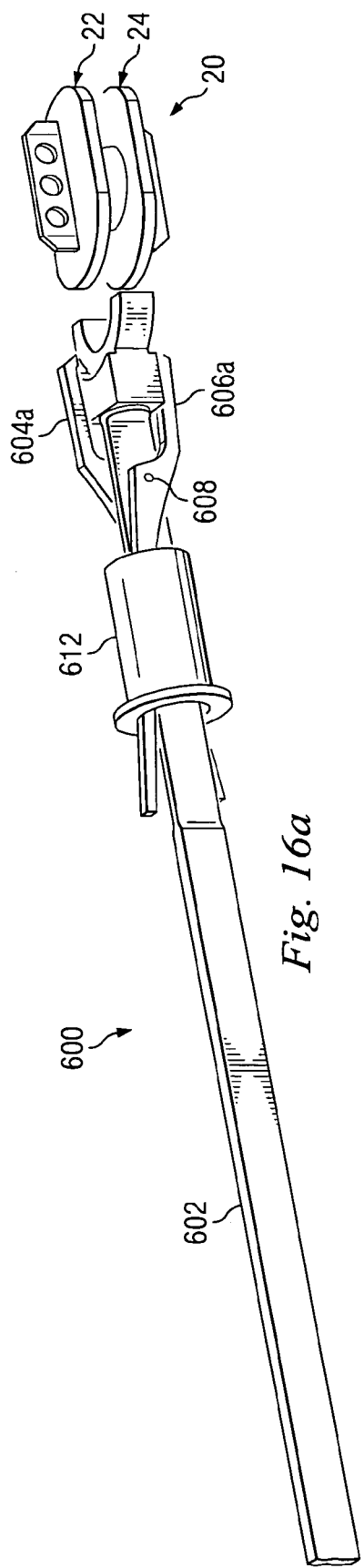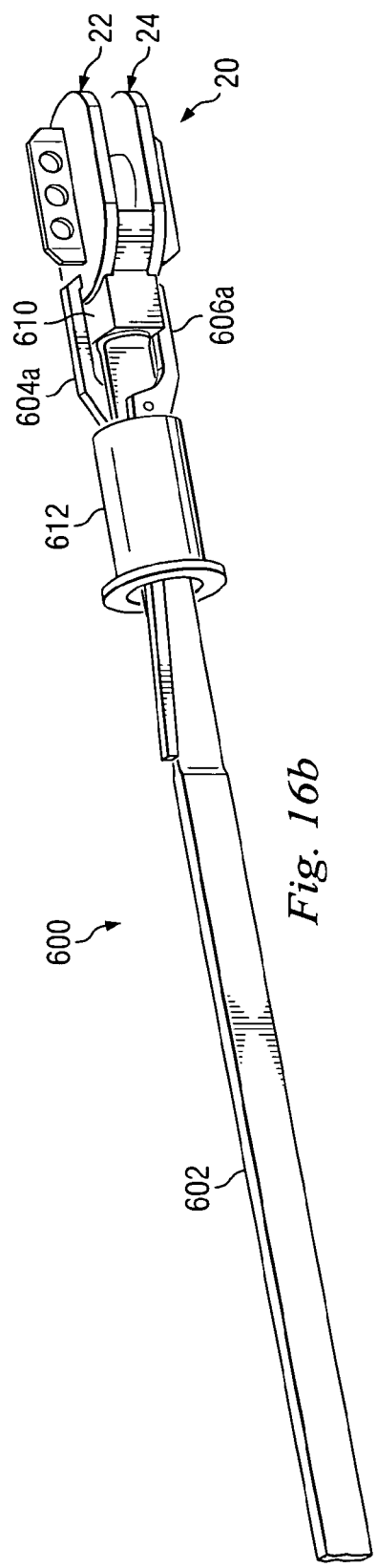
Fig. 16a
Fig. 16b

ARTIFICIAL DISC INSERTER

CROSS-REFERENCE

The present disclosure is a related to U.S. Ser. No. 10/839,100 titled Artificial Intervertebral Disc for Lateral Insertion, filed May 5, 2004 and U.S. Ser. No. 10/773,494 titled Articular Disc Prosthesis for Lateral Insertion, filed on Feb. 12, 2004, both of which are assigned to the same entity as the present patent and are herein incorporated by reference as if reproduced in their entirety.

FIELD OF THE INVENTION

The present disclosure relates generally to the field of orthopedics and spinal surgery, and in some embodiments, the present disclosure relates to a surgical instrument for the insertion of an artificial intervertebral disc.

BACKGROUND OF THE INVENTION

In the treatment of diseases, injuries, or malformations affecting spinal motion segments, and especially those affecting disc tissue, it has long been known to remove some or all of a degenerated, ruptured, or otherwise failing disc. In cases involving intervertebral disc tissue that has been removed or is otherwise absent from a spinal motion segment, corrective measures are taken to ensure the proper spacing of the vertebrae formerly separated by the removed disc tissue. In some instances, prosthetic devices are inserted into the disc space to maintain the structural integrity of the spinal column.

Insertion of prosthetic devices has heretofore been accomplished from an anterior approach to the vertebrae. However, in some regions of the spine, correction from the anterior approach may present difficulties due to the presence of important anatomical structures such as vessels and nerves. For example, the straight anterior approach to the disc space between vertebra L4 and L5, as well as the superior disc levels, can present high surgical risks during the insertion of an implant such as an artificial disc or prosthetic device because of the attachment of the major vessels to the anterior aspect of the spine. Alternatives to correction from an anterior approach are therefore desirable.

Moreover, subsidence of prosthetic devices into adjacent vertebrae has often been a problem due to insufficient contact between the prosthetic device and the appropriate bearing surface provided by the adjacent vertebrae. For example, subsidence of the prosthetic device into the adjacent vertebrae may occur, which can result in a decreased amount of support offered by the prosthetic device. Often, such subsidence is caused by the surgical instruments and/or methods used for inserting the prosthetic device. Surgical instruments often cause or require invasion of the vertebrae and/or other parts of the patient beyond the level of invasion required for the implant itself. For example, the surgical instrument may require removal of additional portions of the vertebral bodies, which can reduce the ingrowth and contact areas and compromise the structural integrity of the vertebral body.

Therefore, what is needed is a surgical instrument for inserting an artificial intervertebral prosthetic device that is simple, stable, and does not compromise the advantages of the artificial intervertebral prosthetic device. Furthermore, what is needed is minimally invasive instrumentation which can be inserted from different approaches. Furthermore, an artificial intervertebral prosthetic device and corresponding instrumentation is needed whereby the window associated with the insertion of the disc is minimized and the bearing contact between the device and the adjacent vertebrae is maximized.

SUMMARY OF THE INVENTION

One embodiment provides an instrument for inserting an implant having a protrusion having a protrusion width for extending into a portion of a vertebral body. The protrusion can be a keel that extends into the end plate of the vertebral body, although other or different protrusions may also exist. The instrument includes an elongated member and a first member connected to the elongated member. The first member has a width substantially equal to or less than the protrusion width and is further adapted for selectively engaging the implant. In some embodiments, the instrument includes a second member in movable communication with the first member for selectively engaging and releasing the implant. In some embodiments, the instrument includes a locking mechanism for holding the first and second members in an engaged position.

In another embodiment, an instrument for inserting a prosthetic device having two components is provided. The first component of the prosthetic device has a first protrusion having a first-protrusion width—for extending into a portion of a first bone structure—and the second component of the implant has a second protrusion having a second-protrusion width—for extending into a portion of a second bone structure. The instrument includes an elongated body having a proximal end and a distal end. A gripping device is connected to the distal end of the elongated body. The gripping device includes a first member having a width substantially equal to or less than the first-protrusion width and adapted for engaging the first component. The gripping device also includes a second member having a width substantially equal to or less than the second-protrusion width and adapted for engaging the second component. In some embodiments the gripping device includes a third member. The third member may be in movable communication with the first member, the second member, or the first and second members for selectively engaging the first component, the second component, or the first and second components, respectively.

In another embodiment, a surgical method is provided. The surgical method includes creating a window to an intervertebral space between adjacent vertebral bodies. An artificial intervertebral prosthetic device having a protrusion, such as a keel, having a protrusion width for extending into a portion of a vertebral body is provided. The implant is inserted through the window into the intervertebral space using a surgical instrument. The surgical instrument includes an elongated body having a proximal end defining a handle and a distal end. A grabbing member having a width substantially equal to or less than the protrusion width is connected to the distal end of the elongated body. The grabbing member is adapted to selectively engage the artificial intervertebral prosthetic device. In some embodiments the surgical method includes selectively engaging the artificial intervertebral prosthetic device and selectively disengaging the artificial intervertebral prosthetic device after insertion. In some embodiments the surgical method includes preparing a cavity in a vertebral body for receiving the protrusion of the artificial intervertebral prosthetic device.

In another embodiment, a kit is provided. The kit includes an implant having a first piece having a first protrusion of a first-protrusion width for engaging a first bone structure and a surgical instrument for inserting the implant. The surgical instrument includes an elongated body having a proximal and distal end. An engagement mechanism is attached to the distal end of the elongated body. The engagement mechanism includes a first member having a first width substantially equal to or less than the first-protrusion width and adapted for selectively engaging the first piece of the implant. The engagement mechanism also includes a second member in movable communication with the first member for selectively engaging the implant. In some embodiments the kit may include an implant that has a second piece having a second protrusion of a second-protrusion width for engaging a second bone structure. In some embodiments the kit includes a plurality of spacers each adapted for interfacing with the engagement mechanism and further adapted for maintaining a spaced relation between the first and second pieces of the implant during engagement.

BRIEF DESCRIPTION OF THE DRAWINGS

FIG. 7b is a lateral view of the arrangement of FIG. 7a.

FIG. 8b is a lateral view of the arrangement of FIG. 8a.

FIG. 9b is a lateral view of the arrangement of FIG. 9a.

FIG. 11a is a perspective view of an alternative embodiment of an implant inserter in a released position according to another embodiment of the present disclosure.

FIG. 10 is a plan view of a portion of an alternative intervertebral disc prosthesis according to another embodiment of the present disclosure.

FIG. 11b is a perspective view of a portion of one embodiment of an implant inserter in a released position.

FIG. 14a is a perspective view of implant inserter of FIG. 13a.

FIG. 16a is a perspective view of an alternative embodiment of an implant inserter in a released position according to another embodiment of the present disclosure.

FIG. 16b is a perspective view of the implant inserter of FIG. 16a in an engaged position with the prosthetic device.

DESCRIPTION

Figure 1:
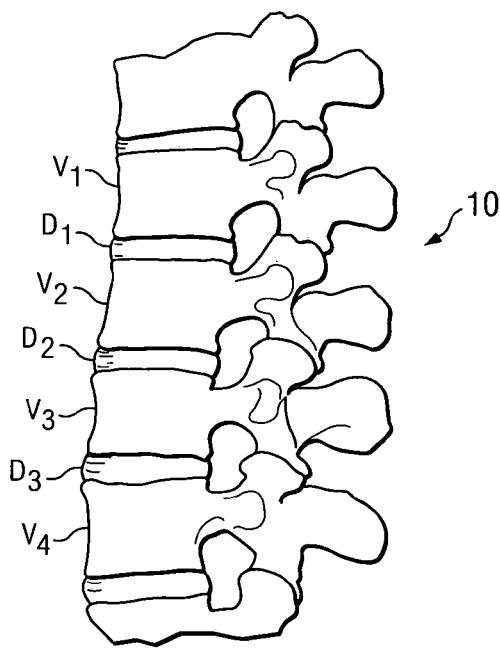
FIG. 1 is a lateral view of a portion of a vertebral column.

This disclosure relates generally to the insertion of artificial prostheses or implants and, in some instances, a surgical instrument for inserting an implant such as an artificial disc or intervertebral prosthetic device. For the purposes of promoting an understanding of the principles of the disclosure, reference will now be made to the embodiments, or examples, illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which this disclosure relates. As such, individual features of separately described embodiments can be combined to form additional embodiments.

Intervertebral Disc Prostheses

Referring now to FIG. 1, shown therein is a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebrae.

Figure 2:
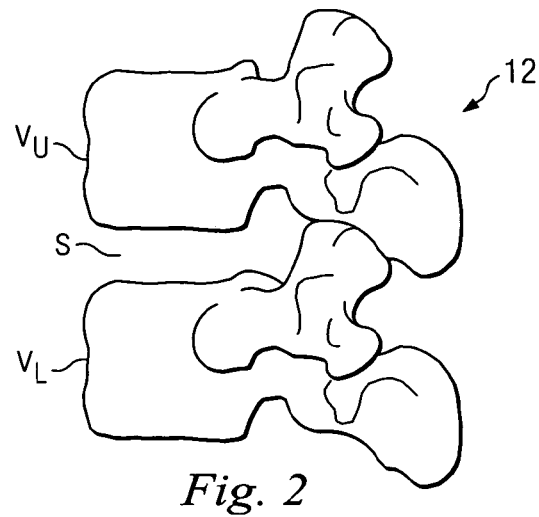
FIG. 2 is a lateral view of a pair of adjacent vertebral bodies defining an intervertebral space.

Referring now to FIG. 2, for the sake of further example, two of the vertebrae will be discussed, designated as a spinal segment 12 including a lower vertebrae $V_L$ and an upper vertebrae $V_U$. In one embodiment, some or all of the natural disc that would have been positioned between the two vertebrae $V_L$, $V_U$ is typically removed via a discectomy or a similar surgical procedure, the details of which would be known to one of ordinary skill in the art. Removal of the diseased or degenerated disc results in the formation of an intervertebral space S between the upper and lower vertebrae $V_U$, $V_L$.

Figure 3:
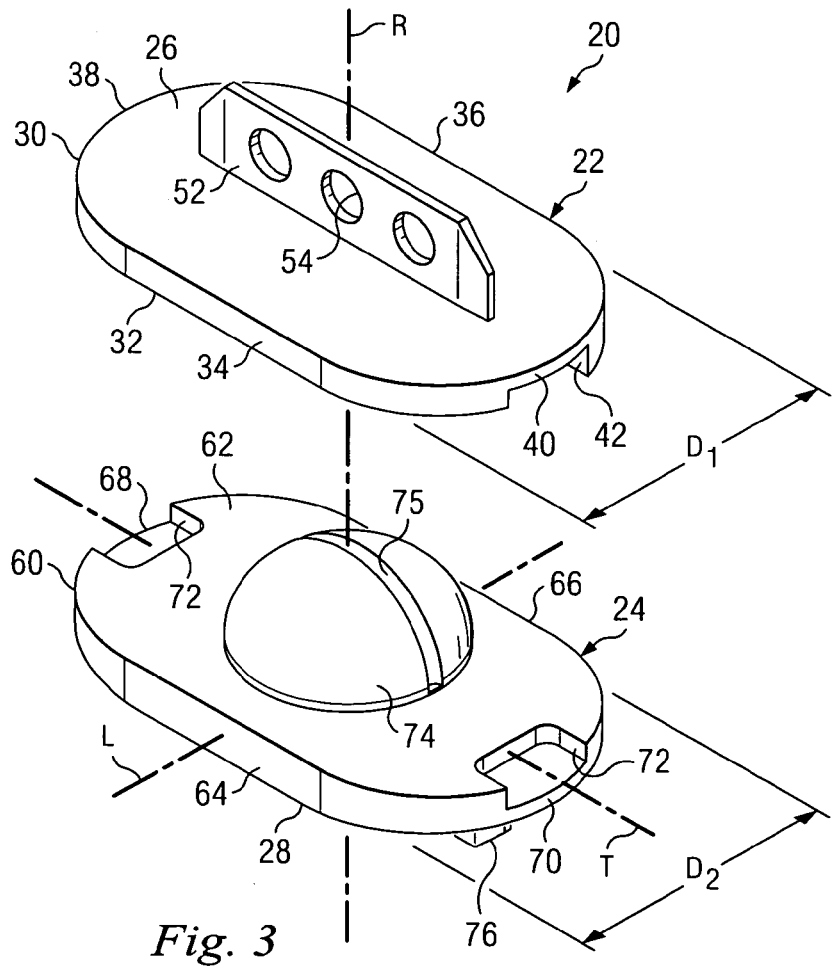
FIG. 3 is a perspective view of an intervertebral prosthetic disc according to one embodiment of the present disclosure.
Figure 4:
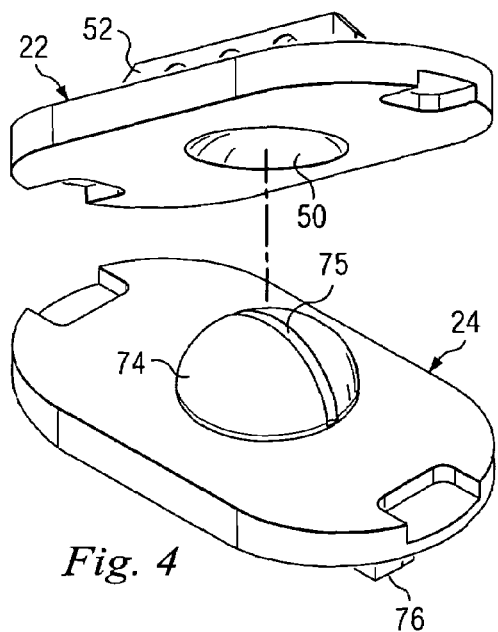
FIG. 4 is a lateral view of the intervertebral prosthetic disc of FIG. 3.
Figure 5:
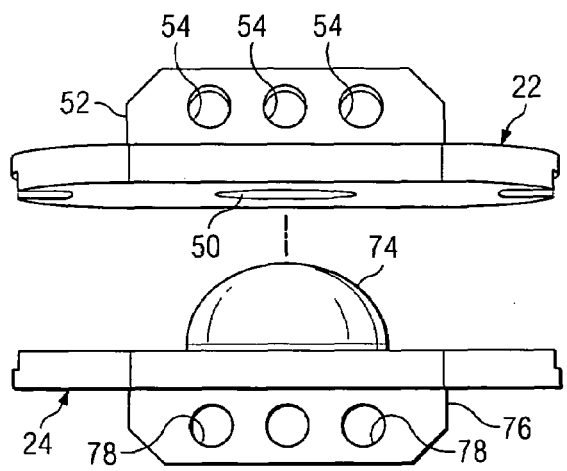
FIG. 5 is a longitudinal view of the intervertebral prosthetic disc of FIG. 3.

Referring now to FIGS. 3-5, shown therein is one embodiment of an intervertebral prosthetic disc 20 for lateral insertion into the intervertebral space S (FIG. 2). In one embodiment, the prosthetic disc 20 provides for articulating motion, thereby restoring motion to the spinal segment defined by the upper and lower vertebrae $V_U$, $V_L$. The prosthetic disc 20 extends generally along a longitudinal axis L corresponding to the anterior-posterior aspect of spinal segment 12 and along a transverse axis T corresponding to the lateral aspect of spinal segment 12.

The prosthetic disc 20 includes a first articular component 22 and a second articular component 24. The articular components 22, 24 cooperate to form the prosthetic disc 20 which is sized and configured for disposition within the intervertebral space S (FIG. 2) between adjacent vertebral bodies $V_U$, $V_L$ (FIG. 2). The prosthetic disc 20 provides relative pivotal and rotational movement between the adjacent vertebral bodies to maintain or restore motion substantially similar to the normal bio-mechanical motion provided by a natural intervertebral disc. More specifically, the articular components 22, 24 are permitted to pivot relative to one another about a number of axes, including lateral or side-to-side pivotal movement about longitudinal axis L and anterior-posterior pivotal movement about transverse axis T. It should be understood that in one embodiment of the disclosure, the articular components 22, 24 are permitted to pivot relative to one another about any axis that lies in a plane that intersects longitudinal axis L and transverse axis T. Furthermore, the articular components 22, 24 are permitted to rotate relative to one another about a rotational axis R. Although the prosthetic disc 20 has been illustrated and described as providing a specific combination of articulating motion, it should be understood that other combinations of articulating movement are also possible, such as, for example, relative translational or linear motion, and such movement is contemplated as falling within the scope of the present disclosure.

Although the articular components 22, 24 of prosthetic disc 20 may be formed from a wide variety of materials, in one embodiment of the disclosure, the articular components 22, 24 are formed of a cobalt-chrome-molybdenum metallic alloy (ASTM F-799 or F-75). However, in alternative embodiments of the disclosure, the articular components 22, 24 may be formed of other materials such as titanium or stainless steel, a polymeric material such as polyethylene, or any other biocompatible material that would be apparent to one of ordinary skill in the art.

The articular components 22, 24 each include a bearing surface 26, 28, respectively, that may be positioned in direct contact with vertebral bone and is preferably coated with a bone-growth promoting substance, such as, for example, a hydroxyapatite coating formed of calcium phosphate. Additionally, the bearing surfaces 26, 28 of the articular components 22, 24, respectively, may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 22 includes a support plate 30 having an articular surface 32 and the opposite bearing surface 26. Support plate 30 is sized and shaped to provide a technically feasible maximum amount of endplate support for the adjacent vertebra $V_U$ (FIG. 2) while minimizing the lateral window associated with insertion of the prosthetic disc 20. For example, the support plate 30 may be shaped such that longitudinal sides 34, 36 of the support plate 30 are substantially parallel and are separated by a distance D1, which corresponds to the lateral window for insertion as will be further described. Additionally, the lateral sides 38, 40 of the support plate 30 may take a curved configuration to correspond to the curvature of the endplate of the adjacent vertebra $V_U$ (FIG. 2). As can be appreciated, the longitudinal sides 34, 36 are elongated relative to the lateral sides 38, 40 to facilitate lateral insertion of the prosthetic disc 20 into the disc space S (FIG. 2). In some embodiments, the ratio of the length of the longitudinal sides 34 or 36 to the width D1 is about 1.3:1 to 1.7:1, with a ratio of about 1.5:1 for the disclosed embodiment.

The support plate 30 may include one or more notches 42 or other types of indicia for receiving or engaging with a corresponding portion of a surgical instrument (not shown) to aid in the manipulation and insertion of the prosthetic disc 20 within the intervertebral space S (FIG. 2) between the adjacent vertebral bodies $V_U$, $V_L$ (FIG. 2).

Referring to FIG. 4, in one embodiment of the disclosure, the articular component 22 includes a recess 50. In one embodiment, the recess 50 has a concave shape, and is configured as a spherical-shaped socket. However, it should be understood that other configurations of the recess 50 are also contemplated, such as, for example, cylindrical, elliptical or other arcuate configurations or possibly non-arcuate configurations. The remaining portion of the articular surface 32 can be angled or otherwise configured to facilitate the insertion and/or use of the prosthesis.

Although the concave recess 50 is illustrated as having a generally smooth, uninterrupted articular surface, it should be understood that a surface depression or cavity may be defined along a portion of the recess 50 to provide a means for clearing out matter, such as particulate debris, that is disposed between the abutting articular components 22, 24.

A flange member or keel 52 extends from the bearing surface 26 and is configured for disposition within a preformed opening in the adjacent vertebral endplate. As with the bearing surface 26, the keel 52 may be coated with a bone-growth promoting substance, such as, for example, a hydroxyapatite coating formed of calcium phosphate. Additionally, the keel 52 may be roughened prior to being coated with the bone-growth promoting substance to further enhance bone on-growth. In one embodiment, the keel 52 extends along the transverse axis T and is substantially centered along the bearing surface 26. However, it should be understood that other positions and orientations of the keel 52 are also contemplated.

In one embodiment, the keel 52 transversely extends along a substantial portion of the articular component 22. Such an embodiment would accommodate insertion of the prosthetic joint 20 using a lateral approach as opposed to, for example, an anterior approach. In a further embodiment, the keel 52 may be angled, tapered, or configured in some other shape to facilitate the functional demands of the keel. In still another embodiment, the keel 52 may be configured as a winged keel, including a lateral portion (not shown) extending across the main body portion of keel 52.

In one embodiment, the keel 52 includes three openings 54 extending therethrough to facilitate bone through-growth to enhance fixation to the adjacent vertebral bodies $V_U$, $V_L$ (FIG. 2). However, it should be understood that any number of openings 54 may be defined through the keel 52, including a single opening or two or more openings. It should also be understood that the openings 54 need not necessarily extend entirely through the keel 52, but may alternatively extend partially therethrough. It should further be understood that the keel 52 need not necessarily define any openings 54 extending either partially or entirely therethrough. Additionally, although the openings 54 are illustrated as having a circular configuration, it should be understood that other sizes and configurations of openings 54 are also contemplated.

Articular component 24 includes a support plate 60 having an articular surface 62 and the opposite bearing surface 28. Support plate 60 is sized and shaped to provide a technically feasible maximum amount of endplate support for the adjacent vertebra $V_L$ (FIG. 2) while minimizing the lateral window associated with insertion of the prosthetic disc 20. For example, the support plate 60 may be shaped such that longitudinal sides 64, 66 of the support plate 30 are substantially parallel and are separated by the distance D2, which corresponds to the lateral window for insertion as will be further described. Additionally, the lateral sides 68, 70 of the support plate 60 may take a curved configuration to correspond to the curvature of the endplate of the adjacent vertebra $V_L$ (FIG. 2). As can be appreciated, the longitudinal sides 64, 66 are elongated relative to the lateral sides 68, 70 to facilitate lateral insertion of the prosthetic disc 20 into the disc space S (FIG. 2). In some embodiments, the ratio of the length of the longitudinal sides 64 or 66 to the width D2 is about 1.3:1 to 1.7:1, with a ratio of about 1.5:1 for the disclosed embodiment.

In some embodiments, support plates 60 and 30 are symmetrical in shape, with distance D1 equal to distance D2. In other embodiments, the plates 60, 30 may be of different sizes and shapes to accommodate different requirements. For example, in some embodiments, distance D1 does not equal distance D2.

The support plate 60 may include one or more notches 72 or other types of indicia for receiving or engaging with a corresponding portion of a surgical instrument (not shown) to aid in the manipulation and insertion of the prosthetic joint 20 within the intervertebral space S (FIG. 2) between the adjacent vertebral bodies $V_U$, $V_L$ (FIG. 2). In one embodiment, the notches 72 are shaped in a manner similar to that of the notches 42.

The notches 42, 72 may be formed to selectively lock or otherwise engage with an insertion-type surgical instrument (not shown). The surgical instrument is preferably configured to hold the articular components 24, 24 at a predetermined orientation and spatial relationship relative to one another during manipulation and insertion of the prosthetic disc 20, and to release the articular components 24, 24 once properly positioned between the adjacent vertebrae. In other embodiments, a combination of holes, apertures, and other mechanisms can be used to engage with various surgical instruments.

In one embodiment of the disclosure, the articular component 22 includes a projection 74 having a convex shape, which may be configured as a spherical-shaped ball (half of which is shown). It should be understood that other configurations of the projection 74 are also contemplated, such as, for example, cylindrical, elliptical or other arcuate configurations or possibly non-arcuate configurations. It should also be understood that the remaining portion of articular component 22 may take on planar or non-planar configurations, such as, for example, an angular or conical configuration extending about the projection 74.

A surface depression or cavity 75 may be defined along a portion of the projection 74 to provide a means for clearing out matter, such as particulate debris, that is disposed between the abutting articular components 22, 24. Of course, in other embodiments, the convex articular surface of the projection 74 may alternatively define a generally smooth, uninterrupted articular surface. In another embodiment, each of the convex projection 74 and the concave recess 50 may define a surface depression to facilitate removal of particulate matter disposed between the abutting articular components 22, 24.

A flange member or keel 76 extends from the bearing surface 28 and is configured for disposition within a preformed opening in the adjacent vertebral endplate. As with the bearing surface 28, the keel 76 may be coated with a bone-growth promoting substance, such as, for example, a hydroxyapatite coating formed of calcium phosphate. Additionally, the keel 76 may be roughened prior to being coated with the bone-growth promoting substance to further enhance bone on-growth. In one embodiment, the keel 76 extends along the transverse axis T and is substantially centered along the bearing surface 62. However, it should be understood that other positions and orientations of the keel 76 are also contemplated.

In one embodiment, the keel 76 transversely extends along a substantial portion of the articular component 24. Such an embodiment would accommodate insertion of the prosthetic disc 20 using a lateral approach as opposed to, for example, an anterior approach. In a further embodiment, the keel 76 may be angled, tapered, or configured in some other shape to facilitate the functional demands of the keel. In still another embodiment, the keel 76 may be configured as a winged keel, including a lateral portion (not shown) extending across the main body portion of keel 76.

In one embodiment, the keel 76 includes three openings 78 extending therethrough to facilitate bone through-growth to enhance fixation to the adjacent vertebral bodies $V_U$, $V_L$ (FIG. 2). However, it should be understood that any number of openings 78 may be defined through the keel 76, including a single opening or two or more openings. It should also be understood that the openings 78 need not necessarily extend entirely through the keel 76, but may alternatively extend partially therethrough. It should further be understood that the keel 76 need not necessarily define any openings 78 extending either partially or entirely therethrough. Additionally, although the openings 78 are illustrated as having a circular configuration, it should be understood that other sizes and configurations of openings 78 are also contemplated.

Figure 6:
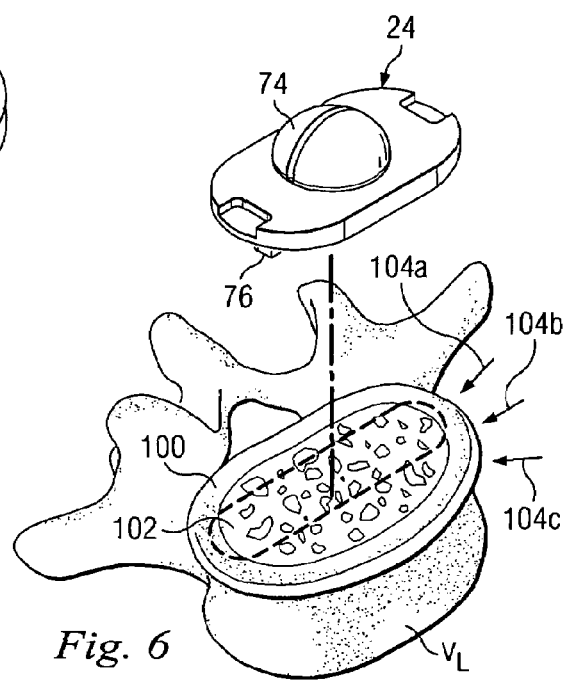
FIG. 6 is a perspective view of a portion of the intervertebral prosthetic disc shown exploded from a vertebral body.

Referring now to FIG. 6, articular component 24 is shown exploded from the lower vertebral body $V_L$. In this example, the natural endplate associated with the lower vertebral body $V_L$ has been removed. However, it is understood that the intervertebral prosthetic disc 20 may be used in situations where the endplate remains intact with the adjacent vertebral body. The vertebral body $V_L$ includes an outer ring of cortical bone 100, often referred to as the apophyseal ring. The inner portion of the vertebral body $V_L$ comprises cancellous bone 102, which is softer and weaker than the cortical bone of the apophyseal ring. The design of the articular component 24, and therefore the intervertebral prosthetic disc 20, facilitates contact between the intervertebral prosthetic disc and the cortical bone 100 of the apophyseal ring, thereby providing an appropriate bearing surface which prevents subsidence of the intervertebral prosthetic disc into the cancellous bone portion of the lower vertebral body $V_L$.

Figure 7A:
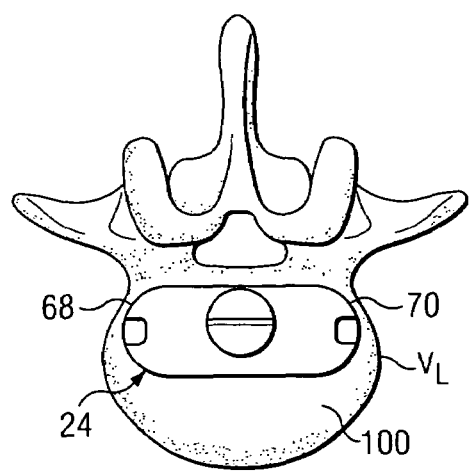
FIG. 7a is a plan view of a portion of the intervertebral prosthetic disc shown laterally disposed in an intervertebral space.
Figure 7B:
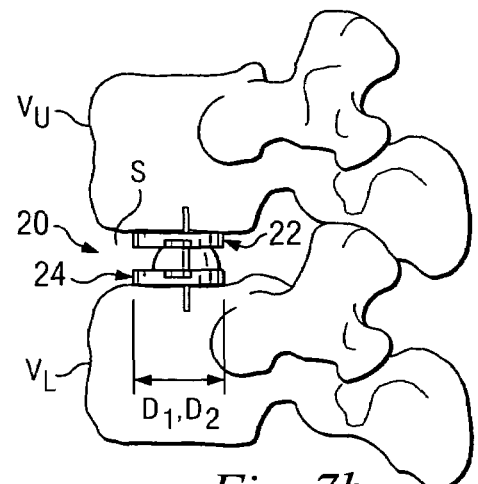

Referring also to FIGS. 7a, 7b, and 7c, the prosthetic disc 20, as represented by the articular component 24, can be inserted from several different lateral approaches 104a, 104b, and 104c. The approach 104a (corresponding with FIGS. 7a, 7b) is a direct lateral insertion trajectory, parallel with the transverse axis T (FIG. 3). The approach 104b (corresponding with FIGS. 8a, 8b) is an oblique insertion trajectory, 10-degree offset from the transverse axis T. The approach 104c (corresponding with FIGS. 9a, 9b) is an oblique insertion trajectory, 20-degree offset from the transverse axis T. The curved shape of the lateral sides 38, 40 and 68, 70 can be chosen to support the different approaches 104a, 104b, 104c so that regardless of the approach, a portion of the corresponding articular components 22, 24 will be suitably positioned above the cortical bone 100 of the apophyseal ring.

For example, referring to FIG. 7a, the articular component 24 is shaped to span the length of the adjacent vertebral body $V_L$ such that the lateral edges 68, 70 of the articular component 24 are nearly or substantially flush with the edges of the vertebral body $V_L$. Accordingly, the articular component 24 has sufficient length so that it bears against a technically feasible maximum amount of the cortical bone 100 for a given lateral window. As such, subsidence of the articular component 24 into the vertebral body $V_L$ can be prevented.

Turning now to FIG. 7b, the lateral window associated with insertion of the intervertebral prosthetic disc 20 into the intervertebral space S (FIG. 2) is generally shown. As can be appreciated, the size of the lateral window generally corresponds to the amount of trauma imparted to the vertebral region during lateral insertion of prosthetic devices. In some embodiments, the lateral window has a width that is substantially equal to the distances D1, D2 for each of the articular components 22, 24 (FIG. 3). Accordingly, by minimizing the width of the intervertebral prosthetic disc 20, the lateral window associated with its insertion is in turn reduced.

Figure 8A:
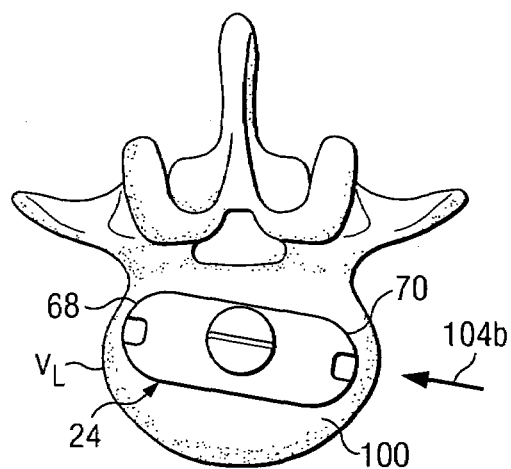
FIG. 8a is a plan view of a portion of the intervertebral prosthetic disc shown laterally disposed in an offset manner in an intervertebral space.
Figure 8B:
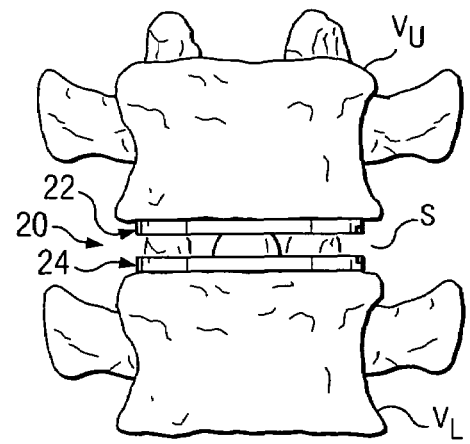

Referring now to FIGS. 8a and 8b, the intervertebral prosthetic disc 20 can be inserted from an oblique approach 104b rather than a direct lateral approach 104a as shown in FIGS. 6, 7a and 7b. In such embodiments, the width of the intervertebral prosthetic disc 20 defined by the distances D1, D2 between the longitudinal sides 34, 36 defines the lateral window for insertion, which again is minimal. Also, even from an oblique approach, the intervertebral prosthetic disc 20 essentially spans the length of the vertebral bodies $V_U$, $V_L$ to bear against an optimal amount of cortical bone of the apophyseal ring.

Figure 9A:
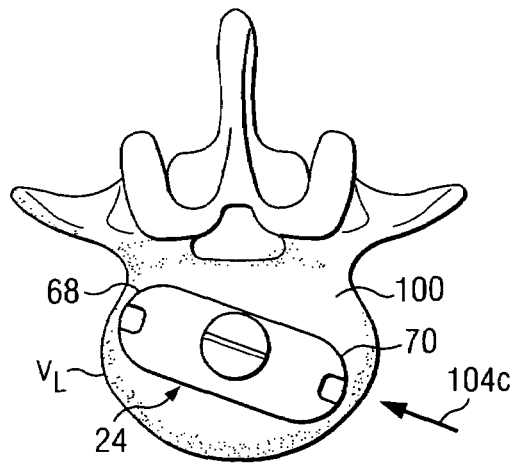
FIG. 9a is a plan view of a portion of the intervertebral prosthetic disc shown laterally disposed in an offset manner in an intervertebral space.
Figure 9B:
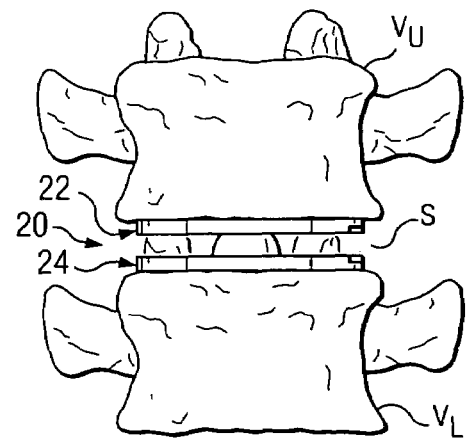

FIGS. 9a and 9b are depicted by way of further example to illustrate that the intervertebral prosthetic disc 20 of the present disclosure can be inserted from the more pronounced oblique angle 104c (FIG. 6) relative to the example, of FIGS. 8a and 8b.

The present disclosure has been described relative to several preferred embodiments. Improvements or modifications that become apparent to persons of ordinary skill in the art after reading this disclosure are deemed within the spirit and scope of the application. For example, different shapes of the intervertebral prosthetic disc according to the present disclosure are contemplated.

Referring to FIG. 10, a portion of an alternative intervertebral prosthetic disc is generally referred to by reference numeral 120. The prosthetic disc 120 includes a first articular component 122 and a second articular component 124. The articular components 122, 124 cooperate to form the prosthetic disc 120 which is sized and configured for disposition within the intervertebral space S (FIG. 2) between adjacent vertebral bodies $V_U$, $V_L$ (FIG. 2). The prosthetic disc 120 provides relative pivotal and rotational movement between the adjacent vertebral bodies to maintain or restore motion substantially similar to the normal bio-mechanical motion provided by a natural intervertebral disc. More specifically, the articular components 122, 124 are permitted to pivot relative to one another about a number of axes, including lateral or side-to-side pivotal movement about a longitudinal axis and anterior-posterior pivotal movement about transverse axis. It should be understood that in one embodiment of the disclosure, the articular components 122, 124 are permitted to pivot relative to one another about any axis that lies in a plane that intersects the longitudinal and transverse axes. Furthermore, the articular components 122, 124 are permitted to rotate relative to one another about a rotational axis. Although the prosthetic disc 120 has been illustrated and described as providing a specific combination of articulating motion, it should be understood that other combinations of articulating movement are also possible, such as, for example, relative translational or linear motion, and such movement is contemplated as falling within the scope of the present disclosure.

Articular component 122 includes a support plate 130 shaped such that longitudinal sides 134, 136 of the support plate 130 are substantially parallel and are separated by the distance D1. Additionally, the lateral sides of the support plate 130 include curved portions 138, 140 that correspond to the curvature of the endplate of the adjacent vertebra $V_U$ (FIG. 2) and straight portions 139, 141. The straight portions 139, 141 are set an angle β of about 60 degrees from the side 134. As can be appreciated, the longitudinal sides 134, 136 are elongated relative to the lateral sides to facilitate lateral insertion of the prosthetic disc 120 into the disc space S (FIG. 2).

Articular component 124 includes a support plate 160 such that longitudinal sides 164, 166 of the support plate 130 are substantially parallel and are separated by the distance D2. Additionally, the lateral sides of the support plate 160 include curved portions 168, 170 that correspond to the curvature of the endplate of the adjacent vertebra $V_U$ (FIG. 2) and straight portions 169, 171. The straight portions 169, 171 are set an angle α of about 60 degrees from the side 164. As can be appreciated, the longitudinal sides 164, 166 are elongated relative to the lateral sides to facilitate lateral insertion of the prosthetic disc 120 into the disc space S (FIG. 2).

Surgical Instruments for Inserting an Implant

Referring now to FIG. 11a, shown therein is one embodiment of a surgical instrument 300 for inserting an implant such as the intervertebral prosthetic disc 20 described above. It is understood, however, that the following discussion can apply to many different types of implants. Although not intended to be limiting, the following discussion will continue to refer to the intervertebral prosthetic disc 20 as an example of an implant that can benefit from the present invention.

The prosthetic disc 20 includes the bearing surface 26 that may be positioned in direct contact with vertebral bone. The protrusion 52, which in the present embodiment is a keel, has a protrusion width $D_3$ and extends from the bearing surface 26. The protrusion 52 is adapted to mate with a preformed opening of a vertebral body. While the protrusion 52 is illustrated as a keel, it is fully contemplated that the protrusion may be of any shape so as to mate with an opening of a bone structure. Other examples of protrusions include spikes, bumps, arches, and ridges.

The surgical instrument 300 includes an elongated member 302 having a proximal end and a distal end. A first member 304 is connected to the distal end of the elongated member 302. The first member 304 is adapted for selectively engaging the prosthetic disc 20. The first member 304 has a width $D_4$ that is substantially equal to or less than the protrusion width $D_3$. The width $D_4$ of the first member 304 is such that the first member can use the preformed opening in the vertebral body to operate.

In the present embodiment, the prosthetic disc 20 may already be located proximate to the final implantation site, such as the space S of FIG. 2. The surgical instrument 300 can then align with the prosthetic disc 20, as illustrated in FIG. 11a, so that the first member 304 aligns with the protrusion 52. Once aligned, a surface of the surgical instrument 300, such as a surface 306 and/or a surface 308, can press against the disc 20 and be used to insert the prosthetic disc 20 into the space S without the need to remove additional portions of the vertebral body. Further, the bearing surface 26 of the prosthetic disc 20 does not need any additional features to be engaged by the first member 304. This allows secure engagement of the prosthetic disc 20 without compromising the ingrowth area. It is fully contemplated, however, that the bearing surface 26 may have additional features, such as, for example, a roughened surface, a coating of bone-growth promoting substance, or other features, that may promote engagement and bone growth by and with the surgical instrument 300.

It is not required that the prosthetic disc 20 be already located proximate to the final implantation site. In some embodiments, selective engagement of the prosthetic disc 20 by the first member 304 may be accomplished in a variety of ways. For example, selective engagement may be accomplished using magnetic force, adhesives, gravity, or any other engagement mechanism using a single member. It is fully contemplated that the surgical instrument 300 may be provided pre-engaged to the prosthetic disc 20. For example, the surgical instrument 300 may be attached to the prosthetic disc 20 using a breakable plastic such that the surgical instrument can be selectively disengaged from the prosthetic disc after insertion. Disengagement may be caused by rotating the surgical instrument 300 about its transverse axis T, thereby breaking the plastic and disengaging the prosthetic disc 20. It should be understood that materials other than plastics may be used to pre-engage the surgical instrument 300 to the prosthetic disc 20. It should be further understood that the materials, including plastics, used to pre-engage the surgical instrument 300 to the prosthetic disc 20 may be scored or perforated to facilitate a cleaner break.

Although disengaging the surgical instrument 300 from the prosthetic disc 20 has been described as rotating the surgical instrument about its transverse axis T, there are other ways to disengage the prosthetic disc. For example, rotating the surgical instrument 300 about its longitudinal axis L or rotational axis R may also disengage or release the prosthetic disc 20. These means of disengagement are contemplated as falling within the scope of the present disclosure. Further, non-rotational means of disengagement are also contemplated as falling within the scope of the present disclosure.

Figure 11C:
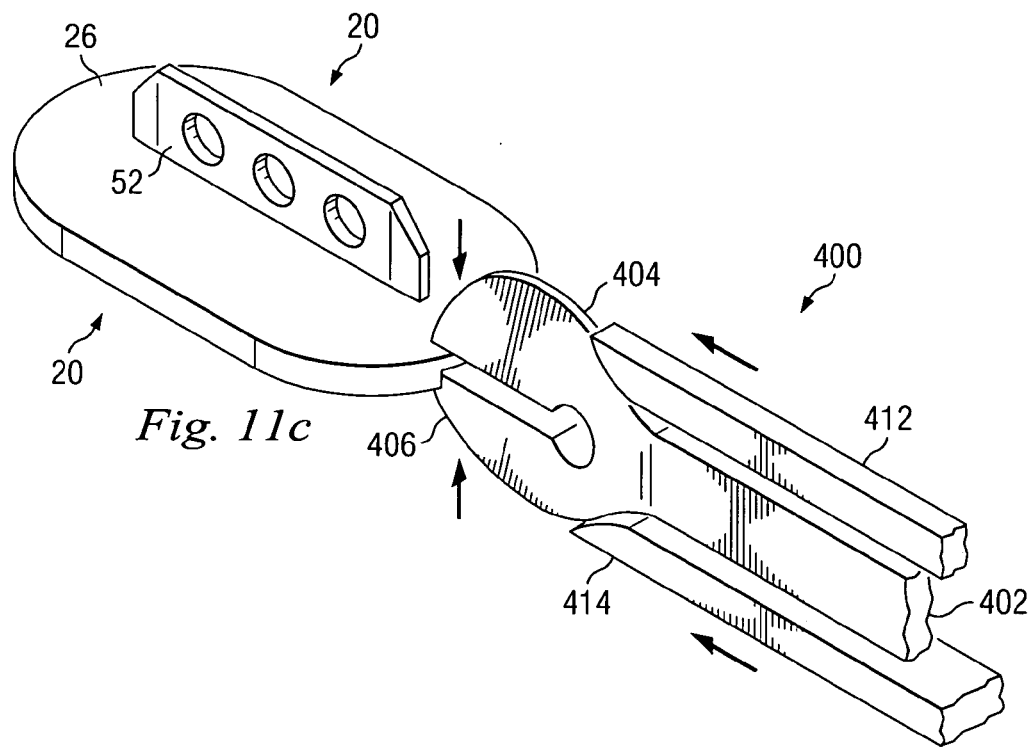
FIG. 11c is a perspective view of the implant inserter of FIG. 11b in the process of engaging the implant.

Referring now to FIGS. 11b and 11c, shown therein is one embodiment of an inserter 400 for inserting the prosthetic disc 20. The inserter 400 includes an elongated member 402 having a proximal end and a distal end. A first member 404 is attached to the distal end of the elongated member 402. A second member 406 is attached to the distal end of the elongated member 402 opposite the first member 404. The second member 406 is in movable communication with the first member 404 for selectively engaging the prosthetic disc 20. The second member includes an engagement surface 408 for interfacing the articular surface of the prosthetic disc 20.

As with the instrument 300 of FIG. 11a, the first member 404 has a width $D_4$ that is substantially equal to or less than the protrusion width $D_3$. The width $D_4$ of the first member 404 is such that the first member can use the preformed cavity in the vertebral body to operate. This allows secure engagement of the prosthetic disc 20 by the surgical instrument 400 without the need to remove additional portions of the vertebral body. Further, the bearing surface 26 of the prosthetic disc 20 does not need any additional features to be engaged by the first member 404. This allows secure engagement of the prosthetic disc 20 without compromising the ingrowth area of the vertebral body. Again it is fully contemplated, however, that the bearing surface 26 may have additional features, such as, for example, a roughened surface, a coating of bone-growth promoting substance, or other features, that may promote bone growth and engagement without compromising the ingrowth area.

In one embodiment the second member 406 and engagement surface 408 of the second member are shaped to mate with an indention or notch 42 of the articular surface of the prosthetic disc 20. By fitting into the notch 42 the second member 406 can prevent unwanted rotation or movement of the prosthetic disc during manipulation and insertion. The engagement surface 408 may include various features to further prevent unwanted rotation and movement of the prosthetic disc 20 during insertion and manipulation.

Figure 12A:
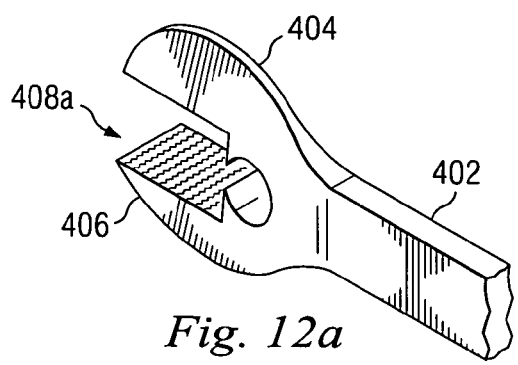
FIG. 12a is a perspective view of a portion of an alternative embodiment of an implant inserter.
Figure 12B:
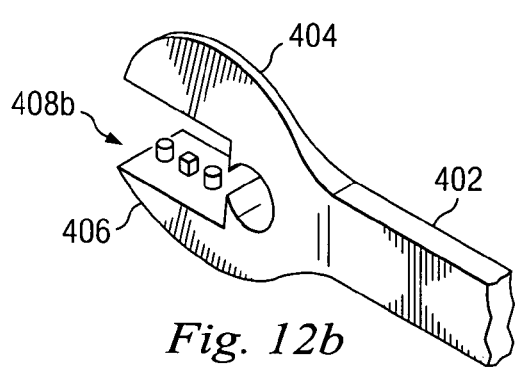
FIG. 12b is a perspective view of a portion of an alternative embodiment of an implant inserter.
Figure 12C:
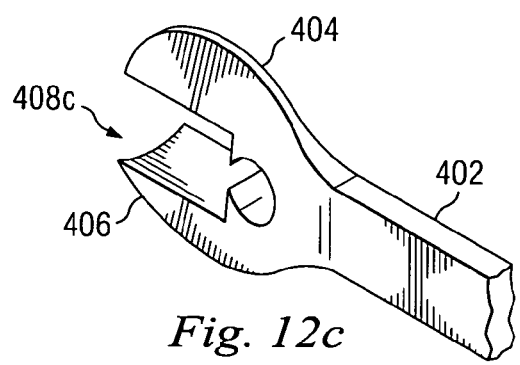
FIG. 12c is a perspective view of a portion of an alternative embodiment of an implant inserter.
Figure 13A:
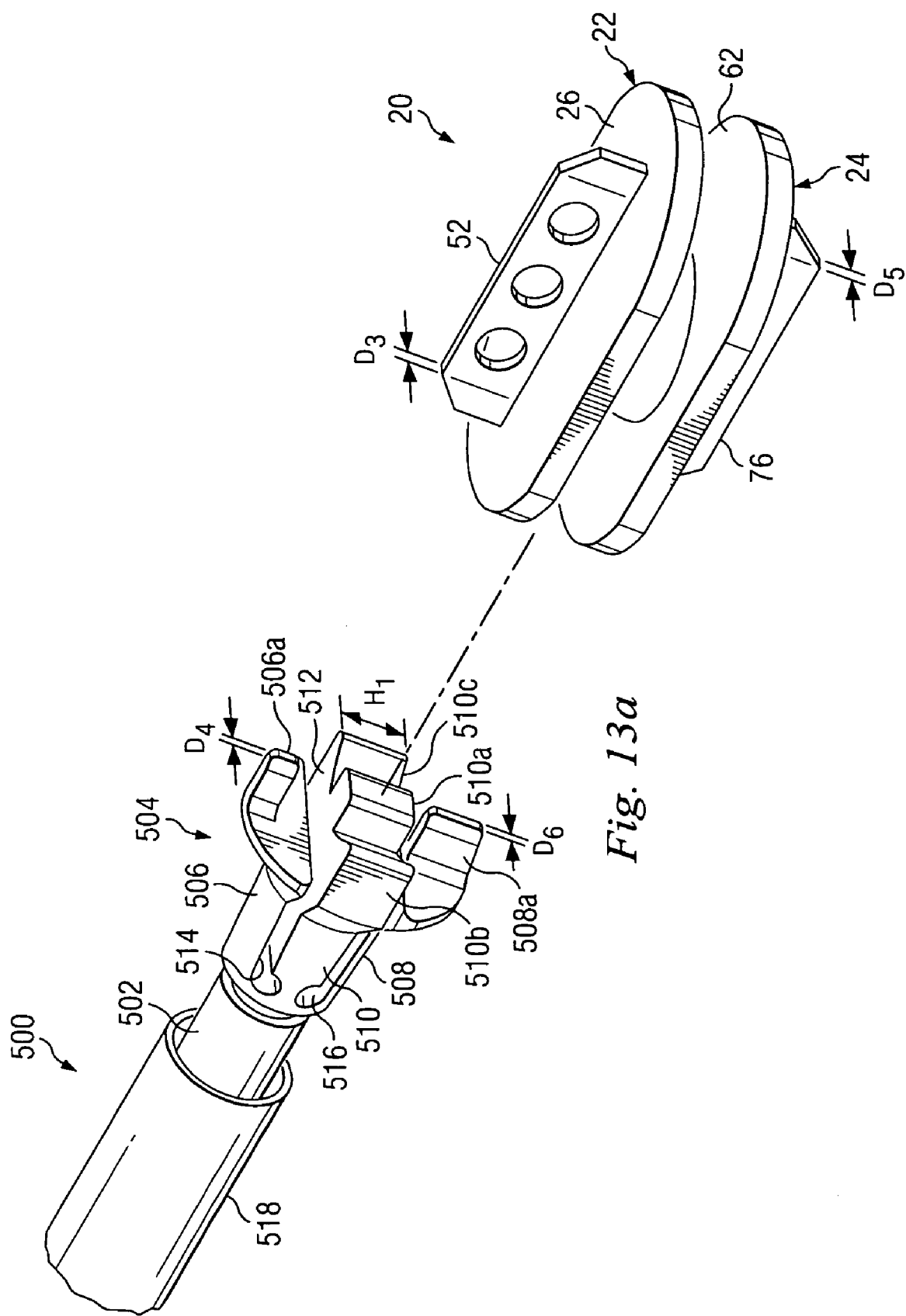
FIGS. 13a and 13b are perspective views of a portion of an alternative embodiment of an implant inserter in a released position and an engaged position, respectively, according to another embodiment of the present disclosure.
Figure 13B:
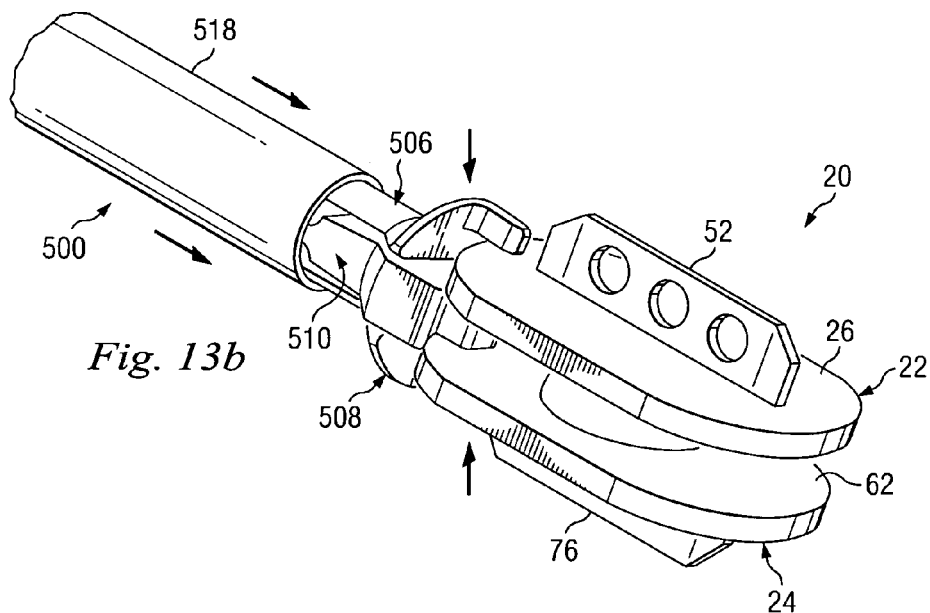
Figure 14A:
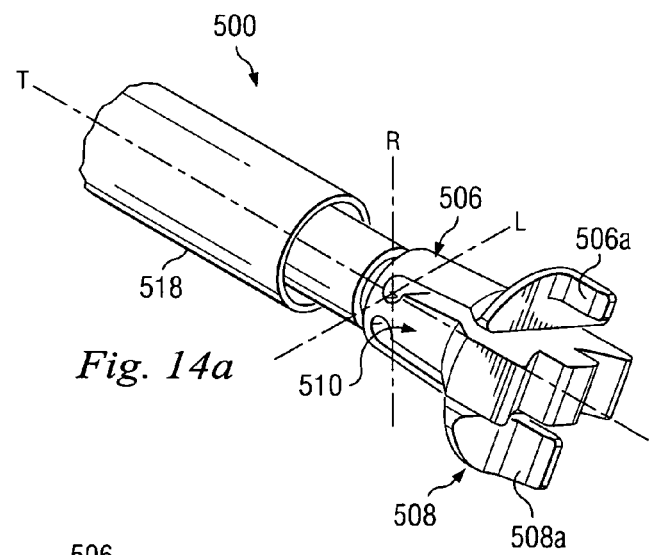
Figure 14B:
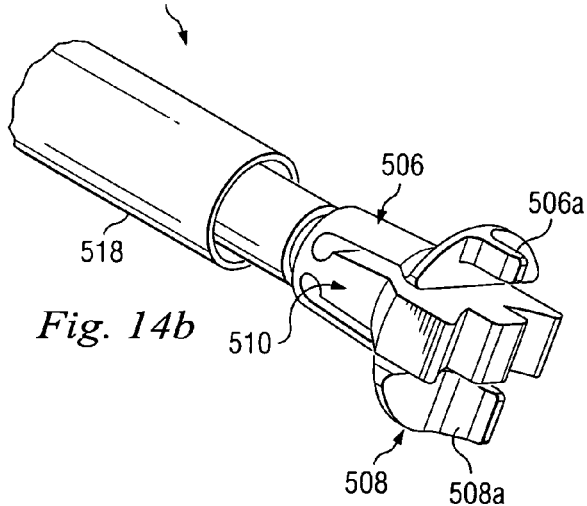
FIG. 14b is a perspective view of an alternative embodiment of an implant inserted with offset portions.

Referring now to FIGS. 12a, 12b, and 12c, shown therein are different modifications to the inserter 400 showing examples of possible surface features and designs that may be used to prevent unwanted rotation and movement of the prosthetic disc. For example, in FIG. 12a the engagement surface $408_a$ is shown as being roughened to prevent slipping. In FIG. 12b the engagement surface $408_b$ is shown having projections designed to engage recesses (not shown) of the articular surface of the prosthetic disc 20. In FIG. 12c the engagement surface $408_c$ is shown having a concave edge designed to engage a corresponding convex surface (not shown) of the notch 42. In other embodiments, a combination of projections, recesses, apertures, and other mechanisms could be used to mate the second member 406 and engagement surface 408 with the prosthetic disc 20.

Referring again to FIGS. 11b and 11c, there are numerous ways for the first and second members 404, 406 to be in movable communication with each other. In one embodiment a pivotal portion 410 provides the means for allowing the first and second members 404, 406 to move with respect to one another. In one embodiment the first and second members 404, 406 are able to move with respect to each other via a fulcrum portion connecting the first and second members to the elongated member 402. It should be understood that other means and mechanisms for putting the first and second members 404, 406 in movable communication with each other are contemplated, including a pin-type engagement.

Further, there are numerous ways to move the first and second members 404, 406 about the pivot point, fulcrum portion, or other movement mechanism to selectively engage the prosthetic disc 20. As illustrated in FIG. 11c the first and second members 404, 406 may be moved by shafts 412, 414, respectively. As the shafts 412, 414 are moved along the elongated member 402 towards the first and second members 404, 406 the first and second members are forced towards each other, thereby grasping or pinching the prosthetic disc 20. The shafts 412, 414 may then be moved away from the first and second members 404, 406 along the elongated member to release or disengage the prosthetic disc.

In another embodiment, the first and second members 404, 406 may be adapted for interfacing with a compression sleeve. In such an embodiment the compression sleeve is used to move the first and second members 404, 406 in a manner similar to the shafts 412, 414 in the previously described embodiment. That is, the compression sleeve is moved along the length of the elongated member to force the first and second members 404, 406 towards or away from each other, thereby, selectively engaging or disengaging the prosthetic disc.

In another embodiment, the first and second members 404, 406 may be adapted for interfacing with a hemostat. The hemostat can be used to create a force to cause the first and second members 404, 406 to move towards or away from each other, thereby, selectively engaging or disengaging the prosthetic disc. Although the movement of the first and second members for selectively engaging the prosthetic disc has been described and illustrated as pinching, grasping, or grabbing the prosthetic disc, it is fully contemplated that other methods of engagement, such as, for example, those described above in relation to surgical instrument 300 are included within this disclosure.

In one embodiment of the disclosure, the surgical instrument 400 includes a locking mechanism for holding the first and second members 404, 406 in an engaged position. Locking the surgical instrument 400 in an engaged position prevents the surgeon, or person using the surgical instrument, from having to concentrate on keeping the prosthetic disc 200 engaged during insertion. Also the locking mechanism can allow free movement of the hand or hands that may be required to keep the surgical instrument 400 in an engaged position. In turn, this can facilitate more precise insertion of the prosthetic disc 20. Once the prosthetic disc 20 has been inserted the locking mechanism can be released for disengagement of the prosthetic disc and removal of the surgical instrument 400. The nature of the locking mechanism will depend on the method of movable communication being used. For each method of movable communication there are a plurality of possible locking mechanisms that are understood as falling within this disclosure.

The surgical instrument 400 may be biased to an engaged position. Similar to a locking mechanism, biasing the surgical instrument 400 to an engaged position prevents the surgeon, or person using the surgical instrument, from having to concentrate on keeping the surgical instrument in an engaged position during insertion and allows free movement of the hand or hands that could be required to keep the surgical instrument in an engaged position. The bias may be created in a variety of ways. Also, the type of bias may depend on the particular method of movable communication being used.

In one embodiment, the first and second members 404, 406 are biased via the pivot point or fulcrum portion to an engaged position. This bias may be created by a single spring or a plurality of springs. In one embodiment, the compression sleeve or hemostat used to move the first and second members 404, 406 is biased towards a particular position, thereby, causing the first and second members to be biased to an engaged position. The bias of the compression sleeve or hemostat may also be caused by the use of springs.

Now referring to FIGS. 13a, 13b, 14a, and 14b, shown therein is one embodiment of a surgical instrument 500 for inserting the prosthetic disc 20. The prosthetic disc 20 has the first component 22 and the second component 24. The first component 22 includes the protrusion 52, having a protrusion width $D_3$, which extends from the bearing surface 26. The protrusion 52 is designed to fit into an opening of a vertebral body. The second component 24 includes the protrusion 76 having a protrusion width $D_5$, which extends from the bearing surface of the second component 24. The protrusion 76 is adapted to fit into an opening of an adjacent vertebral body. Again while the protrusions 52, 76 have been illustrated as keels, it is fully contemplated that the protrusions may be of any shape so as to fit into a cavity of a bone structure. The protrusions 52, 76 may each have a different shape in the same artificial intervertebral prosthetic device. Further, the protrusions 52, 76 may be offset from each other with respect to vertical alignment.

The surgical instrument 500 includes an elongated body or rod 502 having a proximal end and a distal end. A gripping device 504 is connected to the distal end of the rod 502. The gripping device 504 is designed to engage the prosthetic disc 20. The gripping device 504 includes an upper body 506, a lower body 508, and a middle body 510. The upper body 506 is adapted for engaging the bearing surface 26 of the first component 22 of the prosthetic disc 20. The upper body 506 includes a profile 506$_a$ having a width $D_4$ that is substantially equal to or less than width $D_3$ of the protrusion 52. The lower body 508 is adapted for engaging the bearing surface of the second component 24 of the prosthetic disc 20. The lower body 508 includes a profile 508$_a$ having a width $D_6$ that is substantially equal to or less than width $D_5$ of the protrusion 76. The profiles 506$_a$, 508$_a$ of the upper and lower bodies 506, 508, respectively, may be vertically aligned or vertically offset (FIG. 14b) to align with the protrusions 52, 76. It is to be understood that the descriptive labels upper, lower, and middle are in no way intended to the limit the positioning of the components in this disclosure. Rather the use of the labels is a matter of convenience for describing the embodiment.

The width $D_4$ of the upper body and the width $D_6$ of the lower body are such that the upper and lower bodies can use the openings for the protrusions 52, 76 in the respective bone structures to operate. This allows secure engagement of the prosthetic disc 20 without the need to remove additional portions of the bone structures. Further, the bearing surfaces of the first and second components 22, 24 do not need any additional features to be engaged by the upper and lower bodies. Again this allows secure engagement of the prosthetic disc 20 without compromising the ingrowth area. Also it is fully contemplated that additional features promoting bone growth or engagement may be added to the bearing surfaces or upper and lower bodies and remain within the present disclosure.

The middle body 510 includes an upper surface 512 and a lower surface (not shown, but located on the opposing side of the middle body from the upper surface) designed to engage the articular surfaces of the first and second components 22, 24, respectively. The upper and lower surfaces may be shaped and adapted for engaging notches, indentions, projections, recesses, apertures, or other contours of the first and second components 22, 24 of the prosthetic disc 20. Again the labels upper and lower are not intended to limit the positioning the surfaces. The use of labels is simply a matter of convenience.

The middle body 510 may be shaped to maintain a predetermined distance between the first and second components 22, 24. In one embodiment, the middle body has a height $H_1$ representing the desired distance of separation between the first and second components 22, 24. It is fully contemplated that the middle body 510 may have varying heights in a single embodiment to accommodate the shape and contours of the first and second bodies $V_U$, $V_L$. Further, the separation created by the middle body 510 may be designed to accommodate the insertion of a intervertebral disc prosthesis between vertebral bodies in a spondylosed relationship.

In one embodiment, the middle body includes an engagement profile 510$_a$. The engagement profile 510$_a$ may be shaped to mate with any indentions, notches, channels, or other contours of the articular surfaces of the first and second components 22, 24. In this respect, the engagement profile 510$_a$ is designed to help securely engage the prosthetic disc 20 while maintaining the desired space between the first and second components 22, 24. It is fully contemplated that the engagement profile 510$_a$ may be of any shape and have surface features designed to prevent unwanted rotation and movement of the prosthetic disc 20.

The middle body may include guiding profiles 510$_b$, 510$_c$ to prevent unwanted rotation or movement of the first and second components 22, 24 during insertion and manipulation. The guiding profiles 510$_b$, 510$_c$ may be shaped to conform to the contours of the first and second components 22, 24 of the prosthetic disc 20. The guiding profiles 510$_b$, 510$_c$ may be used to help maintain the predetermined space between the first and second components 22, 24. However, it should be understood that the guiding profiles may be used only for preventing unwanted rotation and movement of the prosthetic disc during insertion and still be within the present disclosure.

The surgical instrument 500 includes two pivot points 514, 516 that allow the upper and lower bodies 506, 508 to move in respect to the middle body 510 for selective engagement of the first and second components 22, 24. The pivot points 514, 516 allow a dispersion of forces in a manner that prevents the components of gripping member 504 from breaking without compromising the ability to move. The pivot points 514, 516 may be replaced by a fulcrum or by other movable joints or mechanisms to allow for selective engagement of the prosthetic disc 20. It should be understood that such alternatives to the pivot points 514, 516 are fully contemplated as falling within the scope of the present disclosure.

The surgical instrument 500 includes a compression sleeve 518 for selectively moving the upper and lower bodies 506, 508 with respect to the middle body 510 to engage the prosthetic disc 20. The compression sleeve 518 fits over the rod 502 so that it can slide from an disengaged position (FIG. 13a) to a disengaged position (FIG. 13b), and vice-versa. The surgical instrument 500 may include or be adapted to use a mechanism other than a compression sleeve for engaging the prosthetic disc, for example, a hemostat, and such alternatives are within the present disclosure.

There are several ways the compression sleeve 518 may be manipulated to selectively engage the prosthetic disc 20. In one embodiment the compression sleeve 518 has a length extending along the length of the rod 502 such that a surgeon or other person using the surgical instrument can move the compression sleeve directly, even after insertion. That is, moving the compression sleeve 518 may be accomplished by pushing or pulling on the compression sleeve itself. Moving the compression sleeve 518 then may be used to engage or disengage the prosthetic disc 20. The compression sleeve 518 could be attached to or adapted to interface with a mechanism (not shown) to allow the person using the surgical instrument 500 to engage or disengage the compression sleeve via the mechanism and not the compression sleeve directly. In such an embodiment the mechanism would be accessible to the person using the surgical instrument 500 even after insertion so that the surgical instrument could be disengaged from the prosthetic disc 20.

In another embodiment the compression sleeve 518 may be threaded to the rod 502 such that rotating the compression sleeve about its transverse axis T will move the compression sleeve up or down the rod to engage or disengage the prosthetic disc 20, depending on the direction of rotation. Threading the compression sleeve 518 to the rod 502 provides advantages similar to using a locking mechanism or biasing the surgical instrument 500 to an engaged position. That is, threading the compression sleeve 518 can prevent the surgeon from having to concentrate on keeping the prosthetic disc 20 engaged during insertion and also allows free movement of the hand or hands that may be required to keep the surgical instrument 500 in an engaged position. This, in turn, facilitates more precise insertion of the prosthetic disc 20. In continuation, it should be noted that it is fully contemplated that the surgical instrument 500 may be biased to an engaged position or include a locking mechanism (not shown), including embodiments where the compression sleeve 518 is threaded.

Figure 15A:
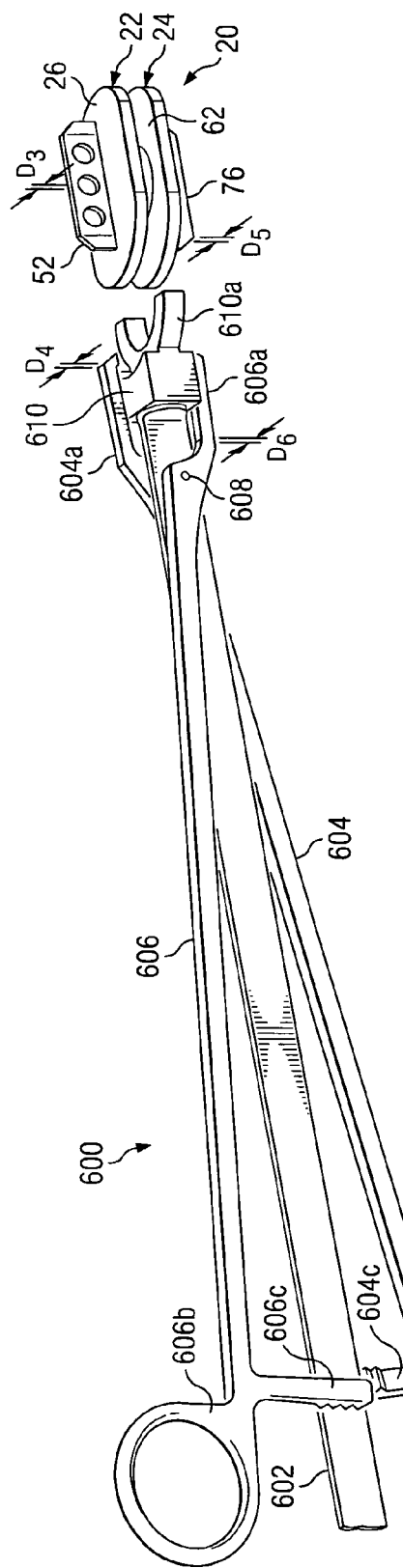
FIG. 15a is a perspective view of an alternative embodiment of an implant inserter in a released position according to another embodiment of the present disclosure.
Figure 15B:
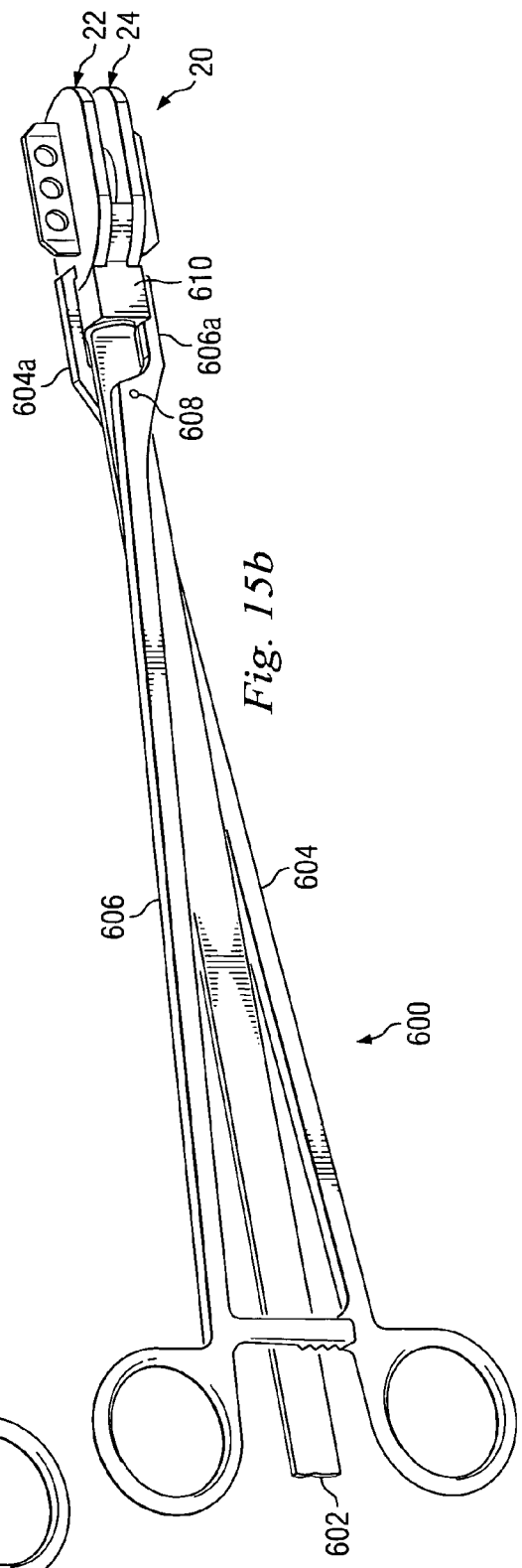
FIG. 15b is a perspective view of the implant inserter of FIG. 15a in an engaged position with the artificial intervertebral prosthetic device.

Referring now to FIGS. 15a and 15b, shown therein is one embodiment of a surgical instrument 600 for inserting the prosthetic disc 20. The prosthetic disc has the components 22 and 24, each with protrusions 52 and 76, respectively. Again while the protrusions 52, 76 have been illustrated as keels, it is fully contemplated that the protrusions may be of any shape so as to fit into a cavity of a bone structure. The protrusions 52, 76 may each have a different shape in the same artificial intervertebral prosthetic device. Further, the protrusions 52, 76 may be offset from each other with respect to vertical alignment.

The surgical instrument 600 includes an elongated body 602 having a proximal and distal end. The surgical instrument 600 includes an engagement member 604. Engagement member 604 has a distal portion $604_a$ adapted for engaging the bearing surface 26 of the first component 22 of the prosthetic disc 20. The distal portion $604_a$ has a width $D_4$ that is substantially equal to or less than the width $D_3$ of the protrusion 52. The engagement member 604 also has a proximal portion $604_b$. The proximal portion $604_b$ may comprise a handle, as in FIGS. 15a and 15b. The engagement member 604 also includes a locking mechanism $604_c$. The locking mechanism $604_c$ may be used to hold the engagement member 604 in an engaged or released position.

The surgical instrument 600 includes an engagement member 606. Engagement member 606 has a distal portion $606_a$ adapted for engaging the bearing surface of the second component 22 of the prosthetic disc 20. The distal portion $606_a$ has a width $D_6$ that is substantially equal to or less than the width $D_5$ of protrusion 76. The engagement member 606 also has a proximal portion $606_b$. The proximal portion $606_b$ may comprise a handle, as in FIGS. 15a and 15b. The engagement member 606 also includes a locking mechanism $606_c$. The locking mechanism $606_c$ may be used to hold engagement member 606 in an engaged or released position. The distal ends $604_a$, $606_a$ of the engagement members 604, 606 may be vertically aligned or vertically offset to align with the corresponding protrusions 52, 76 of the first and second components 22, 24.

Again, the widths $D_4$ and $D_6$ of the distal ends $604_a$, $606_a$ are such that the distal ends can use the openings for the protrusions 52, 76 in the vertebral bodies to operate. This allows secure engagement of the prosthetic disc 20 without the need to remove additional portions of the vertebral bodies. Further, the bearing surfaces of the prosthetic disc 20 do not need any additional features to be engaged by the distal ends $604_a$, $606_a$. This allows secure engagement of the prosthetic disc 20 without compromising the ingrowth area. However, as has been previously mentioned, additional features promoting bone growth or engagement may be added to the bearing surfaces or the distal ends $604_a$, $606_a$ and remain within the present disclosure.

Surgical instrument 600 includes a fulcrum portion 608. Engagement members 604, 606 are connected to the fulcrum portion 608. The fulcrum portion 608 allows the engagement members 604, 606 to move with respect engaged and released positions. As in FIGS. 15a and 15b, the engagement members 604, 606 may be adapted for direct manipulation (e.g. having handle portions). On the other hand, it is fully contemplated that a separate mechanism (not shown) may be used to move the engagement members 604, 606 to engage or disengage the prosthetic disc 20. Also it should be understood that movable joints other than a fulcrum are fully within the present disclosure.

The surgical instrument 600 has a spacer 610 attached to its distal end. The spacer 608 is designed to maintain a predetermined space between the first and second components 22, 24 of the prosthetic disc 20 during engagement (see FIG. 15b). The spacer 610 is adapted to interface with the articular surfaces of the first and second components 22, 24. The spacer 610 may be of various shapes and sizes depending on the predetermined space to be maintained and the form of the prosthetic disc 20. The spacer 610 may be further adapted to prevent unwanted rotation and movement of the prosthetic disc 20 during insertion. For example, the spacer 610 in FIGS. 15a and 15b includes an extended piece $610_a$ to conform to the shape of the prosthetic disc 20 designed to help prevent unwanted movement or rotation and maintain the space between the first and second components 22, 24 of the prosthetic disc.

Referring now to FIGS. 16a and 16b, shown therein is one embodiment of surgical instrument 600. The distal ends $604_a$, 606$_a$ of the engagement members 604, 606 are adapted for interfacing with a compression sleeve 612. The compression sleeve 612 may slide up and down the elongated body 602 to selectively move the engagement members 604, 606, via the fulcrum portion 608, to an engaged position (FIG. 16a) or disengaged position (FIG. 16b). The compression sleeve 612 may be elongated (not shown) to facilitate disengagement of the prosthetic disc 20 after the prosthetic disc has been inserted, at which point it becomes difficult to reach the distal end of the surgical instrument 600. Similarly, the compression sleeve 612 may be adapted to interface a mechanism (not shown) that is easily accessible after insertion and designed to facilitate disengagement once the prosthetic disc 20 has been inserted. The mechanism may be designed to move the compression sleeve 612 to an engaged position as well as being able to disengage the prosthetic disc 20.

Figure 17A:
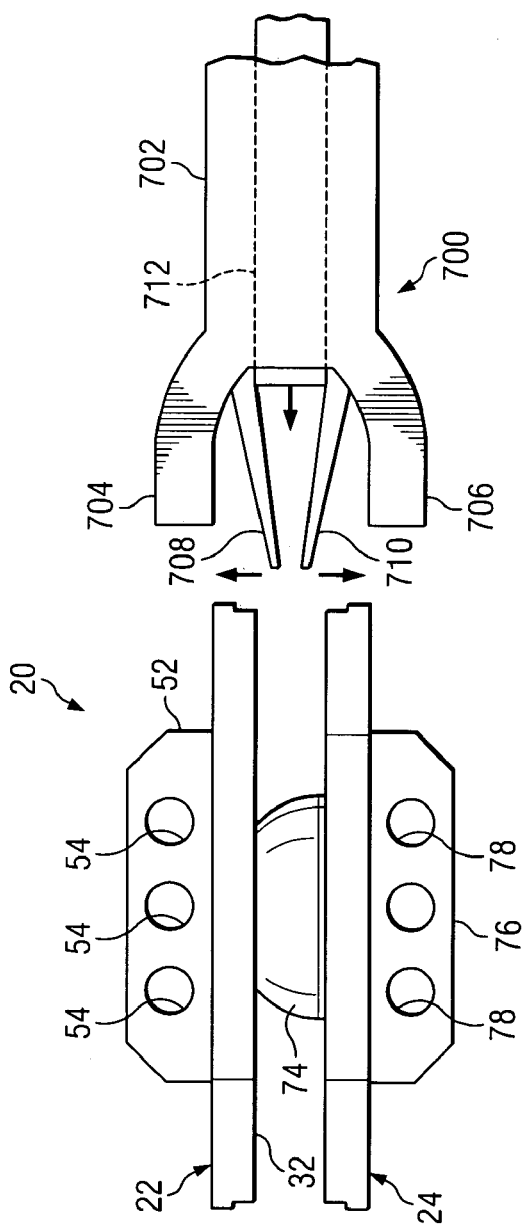
FIG. 17a is a longitudinal view of the cross-section of an alternative embodiment of an implant inserter in a released position according to another embodiment of the present disclosure.
Figure 17B:
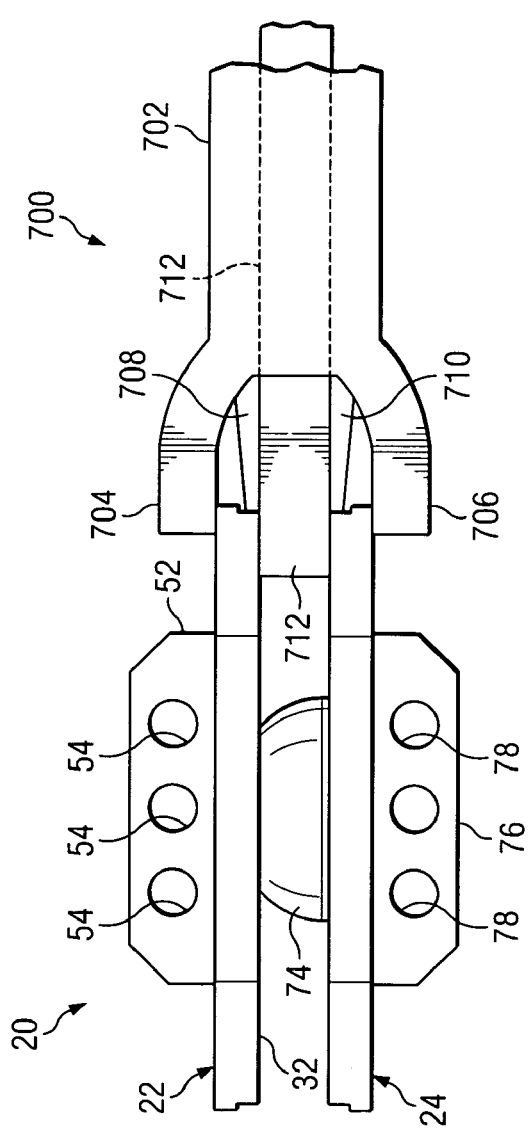
FIG. 17b is a longitudinal view of the implant inserter of FIG. 17a in an engaged position with the disc.

Referring to FIGS. 17a and 17b, shown therein is one embodiment of a surgical instrument 700 for inserting the prosthetic disc 20. The prosthetic disc has the components 22 and 24, each with protrusions 52 and 76, respectively. In some embodiments the protrusions 52, 76 may be offset from each other with respect to vertical alignment.

The surgical instrument 700 includes an elongated body 702 having a proximal end and a distal end. A member 704 is attached to the distal end of the elongated body 702. The member 704 is adapted for engaging the bearing surface of the first component 22 of the prosthetic disc 20. The member 704 has a width $D_4$ that is substantially equal to or less than width $D_3$ of the protrusion 52. A member 706 is attached to the distal end of the elongated body 702. The member 706 is adapted for engaging the bearing surface of the second component 24 of the prosthetic disc 20. The member 706 has a width $D_6$ that is substantially equal to or less than width $D_5$ of the protrusion 76. As in other embodiments, the widths $D_4$ and $D_6$ of the members 704, 706 are such that the members can use the openings created for the protrusions to operate. The members 704, 706 may be vertically aligned or vertically offset corresponding to the alignment of the protrusions 52, 76.

Engagement members 708, 710 are connected to the distal end of the elongated body 702. The engagement members 708, 710 are adapted for interfacing with the articular surfaces of the prosthetic disc 20. The engagement members 708, 710 may have features for mating with the contours (e.g. a notch) of the articular surfaces. In some embodiments the engagement members 708, 710 are designed to prevent unwanted movement and rotation of the prosthetic disc 20 during manipulation and insertion.

A rod 712 is positioned such that it may be introduced into the space between the engagement members 708, 710 to force the engagement members apart. In FIGS. 17a and 17b, the rod is shown as being within the elongated body 702. By inserting the rod 712 into the space between the engagement members 708, 710 the surgical instrument 700 selectively engages the prosthetic disc (FIG. 17b). The rod 712 is sized such that as it is introduced into the space between the first and second engagement members 708, 710 the engagement members are forced apart from each other and towards the first and second members 704, 706, respectively. When the prosthetic disc 20 is present the engagement members 508, 510, with the first and second members 504, 506, will grasp or pinch the prosthetic disc as the rod 512 is pushed into the space between the engagement members. It is fully contemplated that the rod 512 may be biased to an engaged position or combined with a locking mechanism to gain the advantages of introducing a locking mechanisms or bias to the surgical instrument, as previously disclosed.

In one embodiment, a surgical instrument, such as those described above, may be implemented in a surgical procedure for inserting an implant. For example, in one surgical method a window is created to a bone structure. Then an implant having a protrusion for extending into a portion of the bone structure is provided. The implant is inserted through the window and into the bone structure using a surgical instrument, for example, surgical instruments 300, 400, 500, 600, 700, or variations thereof. The surgical method may include selectively engaging the implant before insertion and selectively disengaging the implant after insertion. Further, the surgical method may include preparing a cavity, channel, opening, or other engagement feature in the bone structure for receiving the protrusion of the implant. It is fully contemplated that the surgical method may be used to insert an implant into an intervertebral space between adjacent vertebral bodies. The surgical method may also use a variety of approaches to the intervertebral space, for example, anterior, posterior, lateral, oblique lateral, or any other approach.

The surgical instruments above have been described and illustrated as being used by a surgeon or other person. However, it is fully contemplated that the surgical instruments may be adapted to interface with another mechanism or machine to control its movement. To this effect this disclosure includes any modifications to handles or other aspects of the surgical instruments needed to accommodate the interfacing of another mechanism or machine with the surgical instrument.

In one embodiment, a kit is provided. The kit includes an artificial prosthesis or implant having a first protrusion for engaging a bone structure. A surgical instrument for inserting the implant is also included in the kit. The surgical instrument includes an elongated body having a proximal end and a distal end. An engagement mechanism is attached to the distal end of the elongated body. The engagement mechanism includes a first member adapted for selectively engaging the implant. The first member has a width substantially equal to or less than the width of the protrusion of the implant. The engagement mechanism also includes a second member in movable communication with the first member. The movement allows the first and second members to move with respect to a first position—for engaging the implant—and a second position—for releasing the implant. It is fully contemplated that the surgical instrument may be similar to the surgical instruments described above. Further, it is fully contemplated that the implant in the kit may consist of multiple parts with multiple protrusions for engaging a plurality of bone structures.

The kit may include a plurality of spacers. Each of the plurality of spacers may be adapted to interface with the engagement mechanism. Each of the plurality of spacers may also be adapted to maintain a predetermined distance or space between parts of the implant. Thus, each of the spacers may have a different size and shape. The kit may also include a plurality of implants. Each of the implants may have a different size and shape. It is fully contemplated that there be included various implants corresponding to the various sized and shaped spacers. It is also within this disclosure for the kit to include other surgical instruments, tools, and other materials related to the insertion of prosthetic devices. Further, it is fully contemplated that the kit may include a container for holding all of the other elements of the kit.

It is understood that several modifications, changes and substitutions are intended in the foregoing disclosure and, in some instances, some features of the disclosure will be employed without a corresponding use of other features. It is also understood that all spatial references, such as "inner," "outer," "proximal," "distal," "upper," "lower," and "middle" are for illustrative purposes only and can be varied within the scope of the disclosure. Accordingly, it is appropriate that the appended claims be construed broadly and in a manner consistent with the scope of the disclosure.

What is claimed:

1. An instrument for inserting an artificial disc, the artificial disc including a first component having a first protrusion with a first-protrusion width for extending into a portion of a first vertebral body and a second component having a second protrusion with a second-protrusion width for extending into a portion of a second vertebral body, the instrument comprising:
   an elongated body having a proximal end and a distal end; and
   a gripping device connected to the distal end, the gripping device further comprising:
   a first member adapted to engage the first component, the first member having a first width substantially equal to or less than the first-protrusion width such that the first member does not extend laterally beyond the first protrusion during insertion of the artificial disc;
   a second member adapted to engage the second component, the second member having a second width substantially equal to or less than the second-protrusion width such that the second member does not extend laterally beyond the second protrusion during insertion of the artificial disc; and
   a third member positioned at least partially between the first member and the second member, the first member movable with respect to the third member for movement between a first-component-engaged position for engaging the first component and a first-component-released position for releasing the first component, and the second member movable with respect to the third member for movement between a second-component-engaged position for engaging the second component and a second-component-released position for releasing the second component;
   wherein the first member, the second member, and the third member are portions of a single integral component.

2. The instrument of claim 1 further comprising:
   a first pivotal portion by which a force can be selectively applied to cause the first and third members to selectively engage the first component; and
   a second pivotal portion by which a force can be selectively applied to cause the second and third members to selectively engage the second component.

3. The instrument of claim 1 wherein the third member is further adapted to maintain a spaced relation between the first and second components.

4. The instrument of claim 1 wherein the first and second members are offset from one another in a direction transverse to the length of the elongated body.

5. The instrument of claim 1, further comprising:
   a compression sleeve configured to receive a portion of the first member;
   wherein the first member is adapted to interface with the compression sleeve for selectively moving between the first-component-engaged position and the first-component-released position.

6. The instrument of claim 1, further comprising:
   a compression sleeve configured to receive a portion of the first and second members;
   wherein the first member is adapted to interface with the compression sleeve for selectively moving between the first-component-engaged position and the first-component-released position; and
   wherein the second member is adapted to interface with the compression sleeve for selectively moving between the second-component-engaged position and the second-component-released position.

7. The instrument of claim 1, wherein the first member is biased towards the first-component-engaged position.

8. The instrument of claim 1, wherein the second member is biased towards the second-component-engaged position.

9. The instrument of claim 1, further comprising a locking mechanism for selectively holding the first member in the first-component engaged position and for selectively holding the second component in the second-component engaged position.

10. An instrument for inserting an intervertebral disc prosthesis, the intervertebral disc prosthesis having a first piece having a first keel having a first-keel width on a first exterior surface, the first keel for engaging a superior vertebral body and a second piece having a second keel having a second-keel width on a second exterior surface, the second keel for engaging an inferior vertebral body, the instrument comprising:
    a handle;
    a rod having a proximal end connected to the handle;
    an engagement mechanism connected to a distal end of the rod, the engagement mechanism further comprising:
    a first member for selectively engaging the first piece, the first member having a width substantially equal to or less than the first-keel width;
    a second member for selectively engaging the second piece, the second member having a width substantially equal to or less than the second-keel width;
    a third member having a first surface by which the first member in combination with the first surface can engage the first piece, a second surface by which the second member in combination with the second surface can engage the second piece, and a third surface extending at least partially between the first surface and the second surface for maintaining the first and second pieces in a spaced relation,
    wherein the engagement mechanism is a single integral component.

11. The instrument of claim 10, the engagement mechanism further comprising:
    a fulcrum portion by which a force can be selectively applied to the engagement mechanism to cause the first and second members in combination with the first and second surfaces to engage the first and second pieces, respectively.

12. The instrument of claim 10, wherein the first and second members are movable with respect to the third member between a first position, the first position engaging the first and second pieces and maintaining a spaced relation between the first and second pieces, and a second position, the second position releasing the first and second pieces.

13. A surgical instrument for selectively grasping an implant, comprising:
    an elongated body having a proximal portion, a distal portion, and a longitudinal axis; and
    a gripping portion disposed adjacent the distal portion, the gripping portion comprising
    a central member having a first surface and an oppositely facing second surface;
    a first member extending at least partially in a direction substantially parallel to the longitudinal axis, the first member moveable with respect to the first surface for selectively grasping a first portion of the implant therebetween; and a second member extending at least partially in a direction substantially parallel to the longitudinal axis, the second member moveable with respect to the second surface for selectively grasping a second portion of the implant therebetween, wherein the first member, the second member, and the central member are portions of a single integral component.

14. The surgical instrument of claim 13, further including a compression sleeve disposed concentrically around the elongated body, the compression sleeve adapted for selectively moving the first member toward the first surface for selectively grasping the first portion of the implant.

15. The surgical instrument of claim 14, wherein the compression sleeve is further adapted for selectively moving the second member toward the second surface for selectively grasping the second portion of the implant.

16. The surgical instrument of claim 13, wherein the first and second members are biased towards an engaged position for grasping the first and second portions of the implant.

17. The surgical instrument of claim 13, further comprising a locking mechanism for selectively holding the first and second members in an engaged position for grasping the first and second portions of the implant.

18. The surgical instrument of claim 13, further comprising:
   a first fulcrum portion by which a force can be selectively applied to the gripping portion to cause the first member to move with respect to the first surface for selectively grasping the first portion of the implant; and
   a second fulcrum portion by which a force can be selectively applied to the gripping portion to cause the second member to move with respect to the second surface for selectively grasping the second portion of the implant.

19. An instrument for inserting an artificial disc, the artificial disc including a first component having a first protrusion with a first-protrusion width for extending into a portion of a first vertebral body and a second component having a second protrusion with a second-protrusion width for extending into a portion of a second vertebral body, the instrument comprising:
   an elongated body extending along a longitudinal axis between a proximal portion and a distal portion; and
   an engagement device for selectively engaging the artificial disc extending from the distal portion of the elongated body, wherein the engagement device and the elongated body are portions of a single integral component, the engagement device comprising:
   a first member for engaging the first component, the first member having a first width substantially equal to or less than the first-protrusion width such that the first member does not extend laterally beyond the first protrusion when engaged with the first component of the artificial disc;
   a second member for engaging the second component, the second member having a second width substantially equal to or less than the second-protrusion width such that the second member does not extend laterally beyond the second protrusion when engaged with the second component of the artificial disc; and
   a third member positioned at least partially between the first member and the second member, the third member having a first surface by which the first member in combination with the first surface selectively engages the first component, a second surface by which the second member in combination with the second surface selectively engages the second component, and a third surface extending at least partially between the first surface and the second surface for maintaining the first and second components in a spaced relation when selectively engaging the artificial disc;
   wherein the first member extends at least partially in a direction substantially parallel to the longitudinal axis, the first member movable with respect to the first surface of the third member between a first-component-engaged position for engaging the first component and a first-component-released position for releasing the first component; and
   wherein the second member extends at least partially in a direction substantially parallel to the longitudinal axis, the second member movable with respect to the second surface of the third member between a second-component-engaged position for engaging the second component and a second-component-released position for releasing the second component.

* * * * *

UNITED STATES PATENT AND TRADEMARK OFFICE
CERTIFICATE OF CORRECTION

PATENT NO. : 7,594,919 B2  Page 1 of 1
APPLICATION NO. : 10/898032
DATED : September 29, 2009
INVENTOR(S) : Marc M. Peterman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this

Twenty-eighth Day of September, 2010

David J. Kappos
*Director of the United States Patent and Trademark Office*